United States Patent [19]

Hewitt

[11] 4,057,729
[45] Nov. 8, 1977

[54] MEASUREMENT OF SLURRY CONSISTENCIES

[76] Inventor: John Stringer Hewitt, 89 Nymark Ave., Willowdale-Toronto, Ontario, Canada

[21] Appl. No.: 655,722

[22] Filed: Feb. 6, 1976

[51] Int. Cl.² .............................................. G01T 3/00
[52] U.S. Cl. .................................. 250/390; 250/432 R
[58] Field of Search ........ 250/303, 354, 432, 390–392, 250/356

[56] References Cited

U.S. PATENT DOCUMENTS

| | | | |
|---|---|---|---|
| 3,213,280 | 10/1965 | Burley et al. | 250/391 |
| 3,353,021 | 11/1967 | Stewart | 250/392 |
| 3,577,158 | 5/1971 | Hahn | 250/356 |
| 3,786,251 | 1/1974 | Kylin et al. | 250/390 |
| 3,794,843 | 2/1974 | Chen | 250/392 |

Primary Examiner—Harold A. Dixon
Attorney, Agent, or Firm—Hirons & Rogers

[57] ABSTRACT

Consistencies of aqueous slurries, such as cellulose slurries, are measured by immersing in the slurry a radioactive source of fast neutrons, and neutron detector at a fixed, predetermined distance from the source. The neutron count so obtained can be used to determine slurry consistency. If a second neutron detector is immersed in the slurry at a predetermined, greater distance from the neutron source, the two neutron counts can be used to determine both the slurry consistency and the density of the suspended material.

4 Claims, 4 Drawing Figures

MEASUREMENT OF SLURRY CONSISTENCIES

FIELD OF THE INVENTION

This invention relates to aqueous slurries, and more particularly to processes and apparatus for measuring the amount of solid material contained in an aqueous slurry, i.e., the consistency of the slurry. Its primary application is to measurements of consistency of aqueous slurries of cellulose, e.g., pulpwood-water slurries which are used and handled in the pulp and paper industries.

BACKGROUND OF THE INVENTION

Pulpwood-water slurry is the medium which is subjected to a chemical or mechanical operation in nearly every phase of pulp and paper manufacture. The relative amount by weight of pulp suspended in water, i.e., the consistency of the slurry, is a key parameter which must be accurately monitored and controlled in the efficient operation of such processes as pulping, bleaching, and papermaking. The various plant processes are usually designed around optimal values of consistency. In the interests of economy and quality control, attempts are made to maintain the optimal slurry consistency values throughout the manufacturing plant. Consistency is normally defined as the weight percentage of fibrous material suspended in the slurry. In practice, slurry consistencies in the range from about 1 to about 15% are encountered in commercial pulp and paper operation.

BRIEF DESCRIPTION OF THE PRIOR ART

Instruments commonly used in practice at present for monitoring pulp consistencies are based on the mechanical resistance offered by the slurry to immersed moving objects. Such devices require frequent calibration, because their response mechanism, being based upon mechanical resistance to movement afforded by the slurry, is susceptible to changes in other parameters of the slurry besides the amount of pulp suspended therein. Among such other parameters are temperature, fibre length of the pulp, flow rate, presence in the slurry of added recycle material ("broke"), pressure, wetness, etc.

In addition, the use of such instruments involves the complication of either continuously sampling the flowing slurry stock, or of mounting moving parts within the stock line. Flexibility is also limited by the fact that no single instrument of this type can operate effectively throughout the full range of consistencies encountered in commercial pulp and paper operations.

SUMMARY OF THE INVENTION

It is an object of the present invention to provide a new and improved process and apparatus for measuring the consistency of various types of aqueous slurries.

It is a further object to provide a process and apparatus for measuring slurry consistencies which overcomes or at least reduces one or more of the aforementioned disadvantages.

The present invention is based upon the principle that fast neutrons, as emitted from a radio-active neutron source, are slowed down and diffused in a medium such as an aqueous slurry, the slowing down and absorption of the neutrons being dependent upon the neutron scattering and absorption properties of the nuclei constituting the medium. The most efficient nuclei in an aqueous slurry for causing the slowing down and absorption of neutrons therein are the hydrogen nuclei. The hydrogen nuclei may be present as nuclei of molecules of other substances, or as hydrogen ions. The absorption caused by the presence of other nuclei are of a different order of magnitude, essentially negligible in practice. In water or an aqueous slurry, hydrogen nuclei are present in large numbers. When the material in suspension in the aqueous slurry has smaller numbers of hydrogen nuclei per unit volume than the aqueous suspending medium, the slowing down and absorption capability of a unit volume of slurry is reduced, due to the replacement of some of the hydrogen-nuclei rich water with suspended material in the given volume. The neutron concentration at a given location in the slurry, a fixed distance from the neutron source, is thus related to the consistency of the slurry. Thus by counting the neutrons present in the slurry, at a pre-selected distance from a neutron source in the slurry, a measurement of slurry consistency can be obtained.

The neutron slowing down and absorption caused by the suspended material is also dependent upon the density of the suspended material, as well as its concentration in the aqueous slurry, or consistency. If the density of the suspended material is known, the consistency can be obtained directly by the method and apparatus of the invention. In another aspect, however, the invention provides a method of and apparatus for simultaneously measuring slurry consistencies and densities of suspended material, using a fast neutron source immersed in the slurry, and two neutron detectors placed at two different pre-selected distances in the slurry, from the neutron source.

Thus according to one aspect of the present invention there is provided a process for determining the consistency of an aqueous slurry containing not more than about 15% by weight of suspended material, which comprises:

immersing in the aqueous slurry a fast neutron emitting source;

causing the fast neutrons to slow down and diffuse upon travel within the aqueous slurry;

immersing in the aqueous slurry a neutron detector at a location which is a pre-determined distance from the fast neutron emitting source;

and counting and recording the neutrons detected by the neutron detector at said location in the aqueous slurry.

According to another aspect of the present invention, there is provided an apparatus for determining the consistency of an aqueous slurry, which comprises:

a fast neutron emitting source and at least one neutron detector adapted to be immersed in the aqueous slurry;

the fast neutron emitting source and the neutron detector being located at pre-determined fixed separations from one another;

means for relating the neutron count determined by the neutron detector to the consistency of the slurry passing through the flow vessel.

DESCRIPTION OF THE PREFERRED EMBODIMENTS

Suitable sources of neutron emission for use in the present invention are radioactive polonium-beryllium ($^{210}$Po-Be), and californium ($^{252}$Cf). Such sources emit fast neutrons continuously, at energies in the range of 1–6 MeV. Their migration in a slurry is determined by a combination of two factors. At first, the neutrons are slowed down to thermal energies, of the order of 0.025eV, through a short series of elastic collisions with the light nuclei present in the aqueous slurry, i.e., hydrogen nuclei. On reaching thermal energy, each neutron diffuses through the medium until it is absorbed by a hydrogen nucleus in the slurry. Virtually no absorption of the neutrons by nuclei in the medium occurs until they have been moderated or slowed down to the thermal energy range, which is comparable to the vibrational, etc., energy of the molecules in the medium. Then absorption can occur.

The fast neutrons emanating from an isotropic point source disperse in the medium in all directions. An individual neutron undergoes elastic collision with nuclei in the medium, the collisions causing a reduction in the energy level of the neutron and changes in its direction of travel. After 20 or so such collisions, its energy is reduced to the thermal level. The distance travelled by the neutrons from the source before being moderated by thermal energy can be expressed by a bell-shaped distribution curve, in which distance from the source $r$ is plotted as abscissa (horizontal axis) against number of neutrons per unit time, as ordinate (vertical axis). Such curves are well known in neutron distribution physics, as neutron moderation density distribution kernels.

Once the fast neutrons have been moderated as described, the second factor of neutron distribution takes over, namely that of diffusion and absorption. Now the moderated neutrons undergo collisions with nuclei of the medium, which cause changes in direction of travel of the neutrons and eventually, as a result of a collision, capture of a neutron by a nucleus with which it collides. The distribution of these moderated or "slow" neutrons over the volume of the medium through which they diffuse can again be expressed by a probability distribution curve, in which the population of neutrons detected at a given location is plotted as ordinate (vertical axis) against distance $r'$ of the location from the source of moderated neutrons, as abscissa (horizontal axis). The resulting curve is a bell-shaped distribution curve, known as a thermal neutron diffusion kernal in neutron distribution physics.

In the process of the present invention, however, both the moderation process and the thermal diffusion and absorption process can be considered to be taking place in a given volume of the mdium. The neutron population at a given location in the volume of the medium is a function of the thermal neutron diffusion kernel integrated over all values of $r$, since every location in the volume represents a point of thermalization of a fast neutron and hence a source point of thermal neutrons. The curve of neutron density, or relative neutron flux, against distance from the source of fast neutrons in the given volume is thus a combination, or convolution, of the neutron moderation density distribution kernel and the thermal neutron diffusion kernel. The values necessary to plot such curves can be calculated.

As noted, it is the presence of hydrogen nuclei which causes practically all of the neutron thermalization and diffusion. In the case of aqueous slurries of cellulose pulp, the cellulose has a lower density of hydrogen nuclei than the water. As the consistency of the slurry is increased, more water in a given volume is replaced by cellulose, and so the hydrogen nucleus density of the slurry is reduced. Consequently, an increase in slurry consistency affects the number of neutrons at a given distance from the fast neutron source, since the reduction in hydrogen nucleus concentration means that the average distance travelled by a fast neutron prior to moderation is increased, the thermal neutrons on average travel further in the slurry before being absorbed, and their rate of absorption is decreased by the decreased number of hydrogen nuclei present.

Since the number of hydrogen nuclei per unit volume of the medium exerts the important effect on the neutron density at a given distance from the source, and since this depends on the relative amounts of water and cellulose contained in the unit volume of slurry, it is clear that the density of the cellulose is a factor in the relationship between neutron density and pulp consistency. If the cellulose density is known, the pulp consistency can be readily determined from the neutron flux measurement at a given distance from the neutron source, using a single neutron detector.

According to a preferred embodiment of the invention, however, if two neutron detectors are used, one positioned close to the neutron source and another further from the neutron source, both the slurry consistency and the density of the suspended medium can be obtained, by simultaneous reading of the neutron flux at the two locations. For this purpose, the first neutron detector should be positioned not more than about 9 centimeters from the neutron source and the second neutron detector should be positioned from about 12 to about 20 centimeters from the neutron source, the first and second detectors and the neutron source being immersed in the slurry.

In accordance with the invention, it has been found that there is only one combination of aqueous slurry consistency and suspended solid medium density which can give rise to a given pair of neutron flux readings at two given locations within the above distance ranges from the neutron source.

In the process of the present invention, measurements of neutron flux are being made under equilibrium conditions. The speed fo the neutrons in the slurry is such that an equilibrium situation is established, with a steady rate of fast neutron emission, a steady rate of moderation and a steady rate of absorption to give an equilibrium concentration of neutrons per unit volume as read by the neutron detectors, within the space of about 100 microseconds, subject to the normal statistical fluctuation in counting rate.

DETAILED DESCRIPTION OF A SPECIFIC EMBODIMENT

Figure 1:
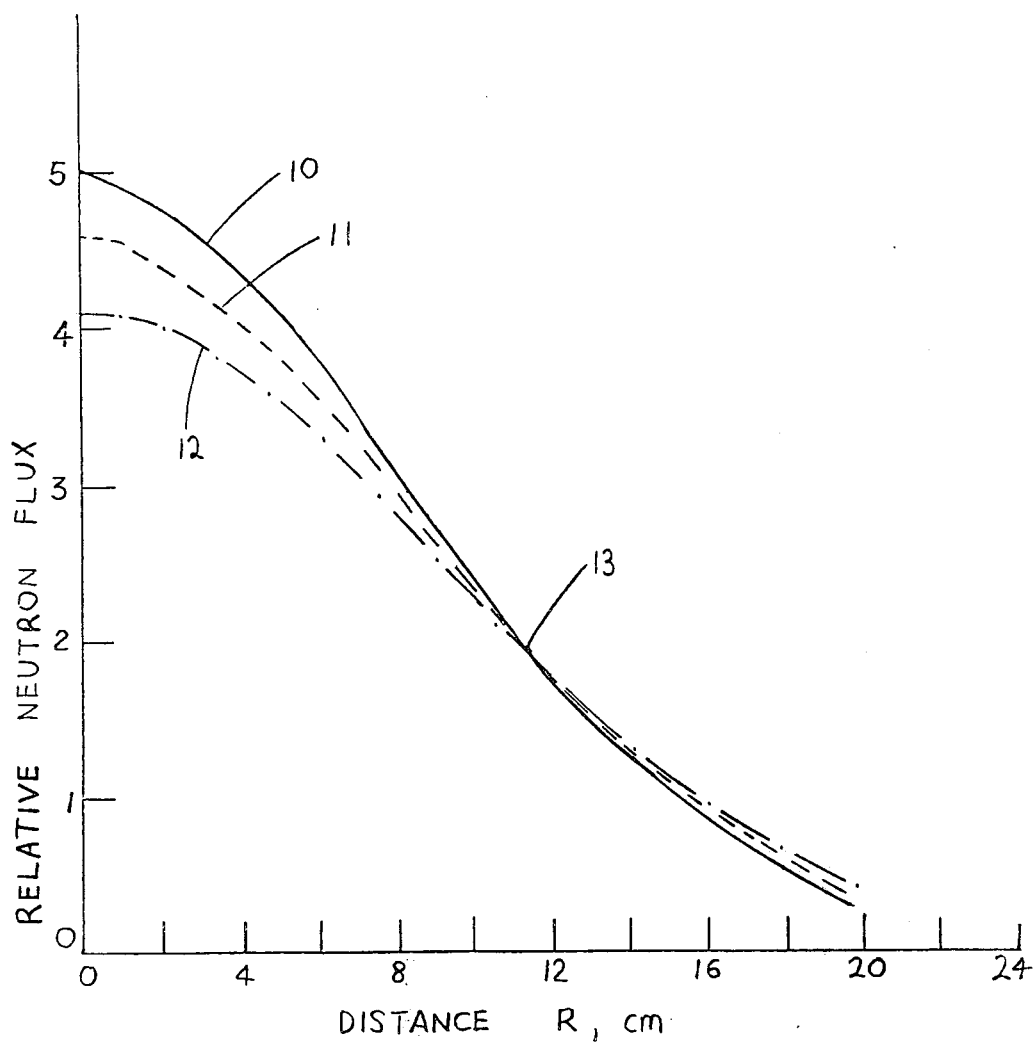
FIG. 1 is a series of curves of relative neutron flux (plotted as ordinate or vertical axis) against distance from neutron source (plotted as abscissa or horizontal axis) constructed from theoretical calculations for an aqueous pulpwood (cellulose) slurry at various consistencies, assuming a give density for the cellulose.

With reference to FIG. 1, this shows the curves which can be theoretically obtained, of neutron flux at various distances up to about 20 centimeters from a fast neutron source in a pulpwood slurry. In effect, these curves are convolutions of the respective neutron moderation density distribution kernels and the thermal neutron diffusion kernels. These curves assume a density of the solid suspended material in the slurry, namely the cellulose, of 0.7 grams per cc. The relative neutron flux is plotted on an arbitrary scale. It will be observed that each individual curve represents a different consistency of the slurry. Curve 10 represents consistency C of zero. Curve 11 represents consistency of 6%. Curve 12 represents consistency of 12%. As noted, these curves can be constructed theoretically by calculations involving knowledge of the density of the solid and liquid constituents of the slurry, their molecular weights, the microscopic cross sections for the nuclei present in the slurry, and various constants. In the alternative, they can be obtained experimentally, by measurements on standard slurries of known consistency, of a material of known density. Using the curves shown in FIG. 1, as the calibration curves, the slurry consistency can be found by measuring the neutron flux with a suitable neutron detector at a given distance from the source, and then locating the consistency curve on which such measured values lie. It is preferred to make such readings at distances from 1 – 8 centimeters from the source, most preferably from 1 – 6 centimeters from the source, since the respective curves vary from one another to the greatest extent in such regions, i.e., a greater dependency of neutron flux on slurry consistency is observed in such regions.

It will be observed that the various curves of FIG. 1 cross over one another, at a point 13 representing a distance about 11 centimeters from the neutron source. At a distance closer to the neutron source, the lower the slurry consistency, the higher the neutron flux or concentration. At a distance greater than the cross over point, the lower the slurry consistency, the lower the neutron flux of concentration. This indicates that, as the consistency increases and the concentration of hydrogen nuclei decreases, the neutrons on average travel further from the source through the slurry before being absorbed by the nuclei — a flatter curve is obtained for slurries of higher consistencies.

Cellulose does not have a constant density, and the density of the pulpwood cellulose present in an aqueous slurry in paper manufacturing processes can vary. Whilst a theoretical i.e., idealized density figure for cellulose is 1.5 grams per cc, this is seldom the actual density of the cellulose present in the pulpwood slurry. This is because surface effects between the cellulose and the water of the slurry come into play, as a result of which the cellulose is not completely wetted by the water, so that its effective density becomes less than the theoretical value. In fact, if the density of the cellulose were the idealized 1.5 value, its presence in an aqueous slurry would have little or no effect upon the hydrogen nuclei density in the slurry, since the higher density of the cellulose as compared with water would effectively compensate for the reduction in the number of hydrogen nuclei in the cellulose as compared with the number in a given volume of water.

The sets of curves of the type shown in FIG. 1 vary according to the density of the cellulose. However, the cross over point 13 of the curves of various consistencies is at approximately the same value, 11 centimeters from the neutron source.

Figure 2:
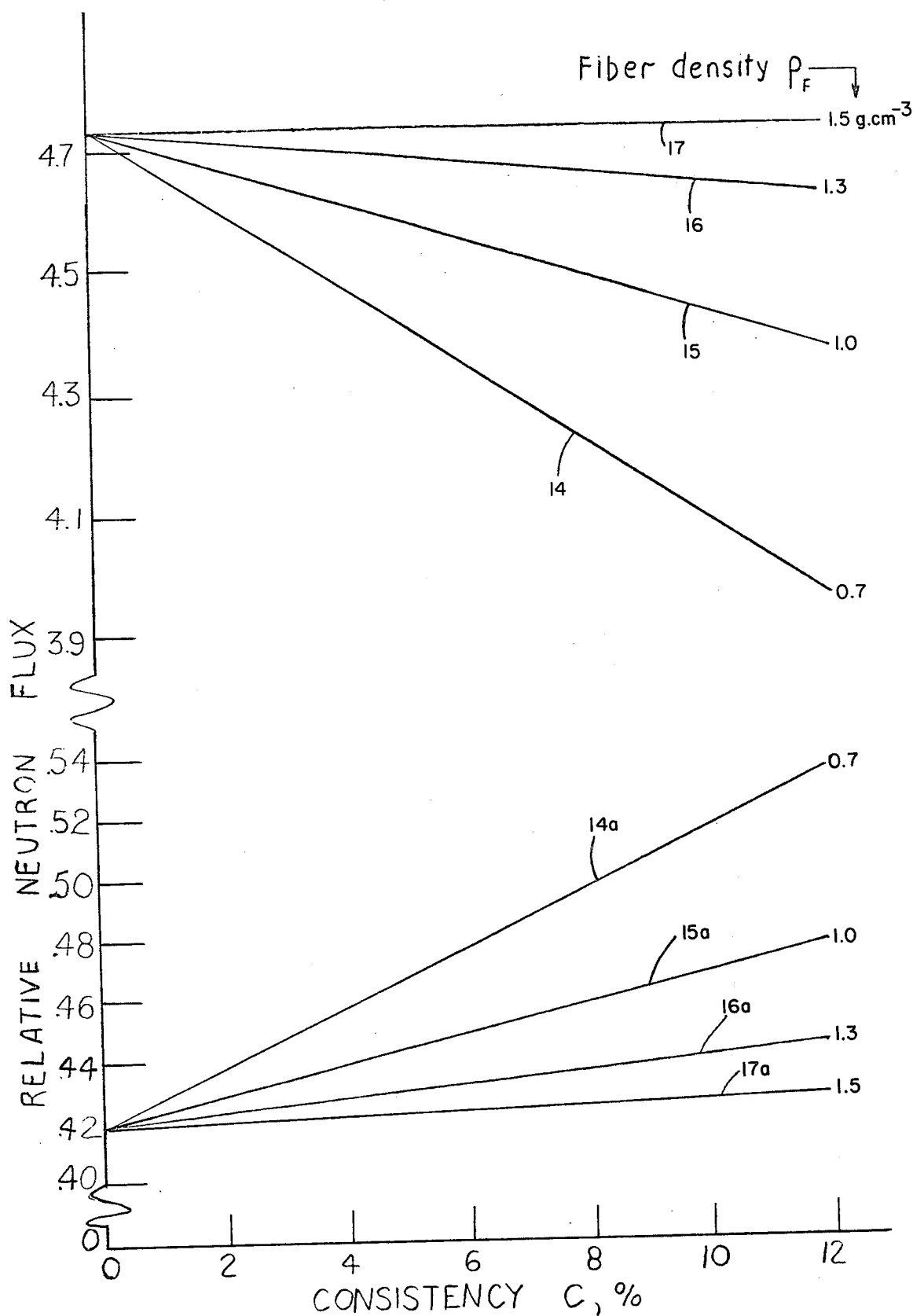
FIG. 2 is a series of curves of relative neutron flux at specific distances from the neutron source (vertical axis) against slurry consistencies, at various densities of cellulose, the upper series representing a first specific distance and the lower series representing a second specific distance.

FIG. 2 shows a series of curves obtained theoretically, from the values on curves such as those on FIG. 1. In constructing the curves of FIG. 2, two fixed values of distance, 2.5 cm. and 18.5 cm. from the neutron source, have been chosen, and relative neutron flux on an arbitrary scale at these fixed distances, is plotted as the vertical axis, and consistency of the pulpwood slurry is plotted as the horizontal axis. The curves now exist in pairs 14 and 14a for example, each pair representing a given density of cellulose suspended in the slurry. The first one of each pair, at the upper portion of FIG. 2, namely curves 14, 15, 16 and 17 represents the readings obtained at a distance of 2.5 cm. from the neutron source. These, therefore, are points from the upper parts of the curves of FIG. 1. These curves of neutron flux against consistency for given density of suspended material are substantially linear, having a negative slope. The lower ones of each pair, namely 14a, 15a, 16a and 17a are taken at a distance of 18.5 cm. from the neutron source, and therefore belong to the lower portions of the curves of FIG. 1. These also shown a linear relationship between neutron flux and consistency, at a given density of suspended material, but having a positive slope.

It turns out from these curves that, any given pair of neutron flux values as measured by a pair of detectors in the slurry, at the fixed distances of 2.5 cm. and 18.5 cm, must correspond to a given density value and a given consistency value, found by locating the appropriate curve on FIG. 2 which the two determined values intersect in vertical alignment, corresponding to a fixed consistency. It is of course known that the two readings taken must correspond to a pulp of the same consistency, since the readings are obtained from the same sample of slurry. Therefore the two points are in vertical alignment on the curves of FIG. 2, and the point where this vertical alignment of the two values of neutron flux density intersects a density curve gives both the consistency and the density of the sample under consideration.

It will be appreciated that it is not necessary to choose the precise pair of values 2.5 cm and 18.5 cm for the distances of the neutron detectors from the neutron source in the slurry. These are examples only. The first value should be chosen from the region of the curves of FIG. 1 above the cross-over point 13, and the second value from the region of curves of FIG. 1 below the cross-over point 13. As shown in FIG. 1, these distances should be, firstly, up to about 9 centimeters, preferably from 1 – 8 centimeters, and secondly 12 – 20 centimeters, preferably 14 – 20 cm. These curves of the form shown in FIGS. 1 and 2 thus comprise a means for relating the neutron count determined by the neutron detectors at fixed separations from the neutron source, to the consistency of the pulp and the density of the suspended material. The counting rate in one detector may be taken as a measure of consistency at a given fibre density. The ratio of the counting rates for the two detectors may be taken as a measure of fibre density at constant consistency.

Figure 3:
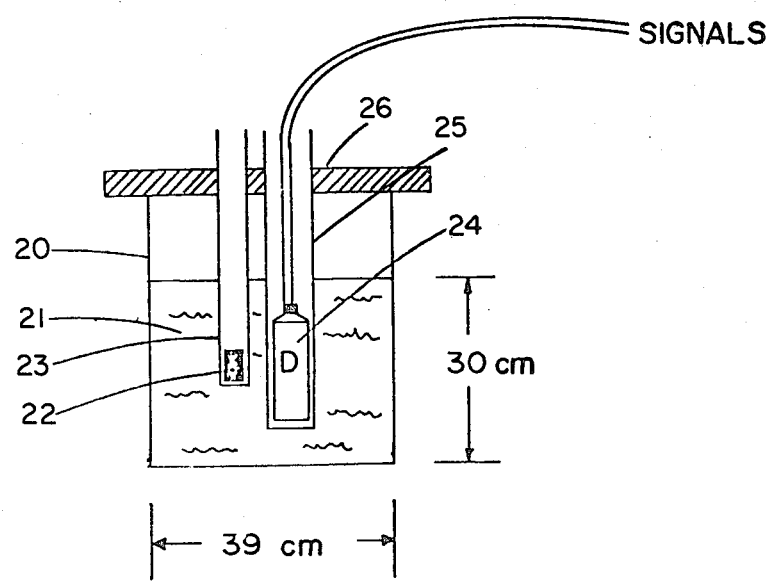
FIG. 3 shows diagrammatically in cross section an apparatus for determining pulp consistency in accordance with the present invention, on a batch sample basis.

With reference to FIG. 3, this shows diagrammatically in cross-section an apparatus for determining pulp consistency in accordance with the invention, on a batch sample basis. The apparatus comprises a cell 20 of circular cross-section containing a quantity of pulpwood slurry 21 to be measured. A radioactive source of fast neutrons 22, namely an americium-241-beryllium neutron source of nominal strength equal to $10^7$ neutrons per second, is positioned in the cell 20, the diameter of which is 39 cm as shown. The cell is filled with slurry to the 30 cm. level. The source 22 is contained in a blind ended plastic pipe 23. A neutron detector 24 in a blind ended plastic pipe 25 is positioned in the cell a fixed, predetermined distance from the source 22. The neutron detector 24 is a boron trifluoride proportional detector enriched in boron-10. Both the source 22 and the detector 24 are rigidly supported in the cell 20, by mounting their respective pipes 23, 25 firmly in a removable cover plate 26. Standard nuclear electronic modules, not shown, can be used to amplify, discriminate and count the neutron pulses generated by the detector.

In experiments conducted using the apparatus shown in FIG. 1, from which the previously described calibration curves can be obtained using slurries of known characteristics, or following such calibration in which slurries of unknown consistency can be measured, counts observed in one minute are of the order of $2.5 \times 10^6$. Data obtained from a series of slurries of consistency up to 3% show that the relationship between counting rates and consistency is linear and can be expressed as counts per second $= 46{,}000 - 2{,}100 \times C$, where $C$ represents the percentage consistency.

Figure 4:
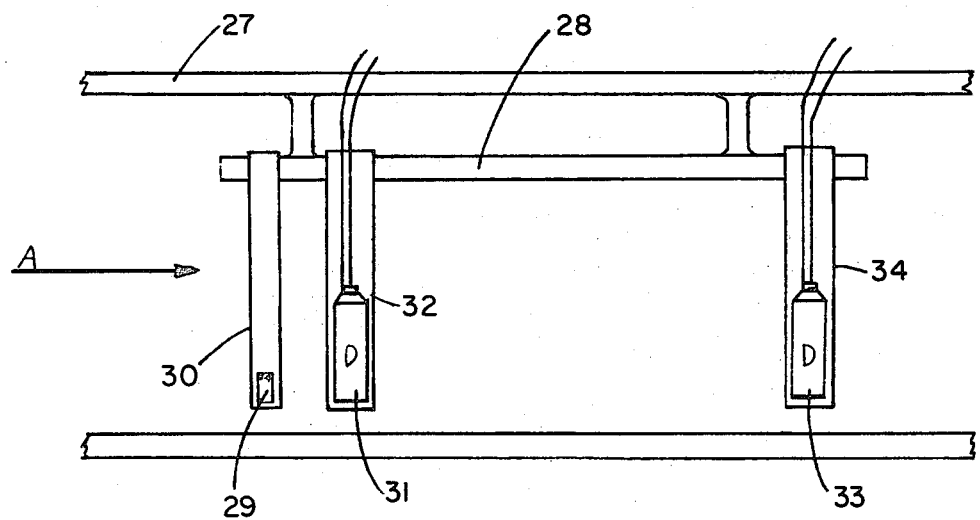
FIG. 4 shows diagrammatically an apparatus according to the invention for use in continuous pulpwood slurry monitoring in a slurry flow conduit.

With reference to FIG. 4, this shows diagrammatically an apparatus according to the invention in use for continuous slurry consistency monnitoring. The apparatus is removably mounted in a slurry flow pipe 27, through which an aqueous slurry is flowing in the direction of arrow A. The apparatus comprises a spacer mounting bar 28 releasably secured to the walls of the slurry pipe 27. The spacer bar 28 carries a neutron source 29 mounted in a plastic tube 30. It also carries a first neutron detector 31 mounted in a plastic tube 32, fixed a short distance from the neutron source 29, and a second neutron detector 33 in a plastic tube 34, positioned a greater distance from the neutron source 29. The respective plastic tubes 30, 32 and 34 are securely mounted in apertures in the spacer bar 28, so that they are fixed distances from one another. The neutron detectors are connected to suitable standard nuclear electronic modules, for amplification, discrimination and counting of the neutron pulses. The neutron source and the neutron detectors can be of generally the same form as those described in connection with the batch measuring apparatus of FIG. 3.

By determination of the neutron flux using the detectors 31, 33 and a measurement of the distances between the neutron source and the first detector, and the neutron source and the second detector, consistency of the slurry and density of the fibers in the slurry flowing through pipe 27 can be monitored continuously, using the suitable calibration curves, as previously described.

It will be apparent that other configurations of apparatus besides that illustrated in FIG. 4 can be constructed and used according to the invention, the form illustrated being by way of example only. The essential features are a fast neutron source, a first detector positioned a given, fixed distance (about 1-8 cm.) from the source, and a second detector positioned a given, fixed distance (about 12-20 cm) from the source.

It will be appreciated that the process of the invention is based upon the two effects exerted on the fast neutrons in the slurry, namely the initial slowing down or thermalization of the neutrons, and the subsequent diffusion and absorption of the thermal neutrons following their thermalization. In the regions close to the neutron source, i.e., the region of the curves of FIG. 1 above the cross-over point 13, the relative neutron flux picked up by the detector is determined primarily by the first effect, whereas the second effect primarily determines the relative neutron flux in the regions further from the source. The simultaneous determination of density and consistency, as noted above, depends upon the ratio of neutron flux and these distances from the source. The sensitivity of the method and apparatus according to the invention, and hence the accuracy of measurement, can be enhanced therefore by taking further steps to separate the regions in which the two different effects predominate, or making the predominance of one effect in a given region more marked. This can be done by varying the geometry of the measuring apparatus, or by adding to the system an absorber for the thermal neutrons, so as to invoke parasitic absorption of the thermal neutrons.

Whilst the invention has been particularly described with reference to pulpwood slurry measurements, it will be appreciated that it is not limited to such applications, but can be used to advantage in measuring slurries of other hydrogenous materials in water or other hydrogenous suspending media, as found in mineral processing and chemical plants. The invention enables slurry consistencies to be measured with greater accuracy, speed and efficiency than those methods previously employed on a commercial scale in the pulpwood industries.

Examples of types of fast neutron sources and neutron detectors have been described in the foregoing description. It will be apparent to those familiar with this field that other types of sources, detectors, and mounting materials as currently available, can be substituted in the method and apparatus of the invention.

It is to be understood that the embodiments of the invention described herewith in detail are exemplary and illustrative only, and that the scope of the invention is not to be considered as limited thereto, but only as defined in the appended claims.

I claim:

1. A process for determining the consistency of a hydrogenous slurry containing not more than about 15% by weight of suspended material, and the density of the suspended material, which comprises:
   immersing in the slurry a fast neutron emitting source;
   causing the fast neutrons to slow down, diffuse and be absorbed by the slurry upon travel within the slurry;
   immersing in the slurry a first neutron detector at a predetermined distance of from 1-8 cm. from the fast neutron emitting source, and a second neutron detector at a predetermined distance of from 12-20 cm. from the neutron source;
   counting and recording the neutrons detected by said first and second neutron detectors at their respective predetermined locations in the slurry;
   determining the slurry consistency and density of the suspended material from the neutron counts recorded at said locations in the slurry.

2. The process of claim 1 wherein the slurry is an aqueous cellulose slurry.

3. The process of claim 1 wherein the slurry is flowing continuously past the neutron source and neutron detectors during said counting and recording.

4. Apparatus for determining the consistency of a slurry having a consistency of up to 15%, and for determining the density of the suspended material in said slurry, which comprises:
- a fast neutron emitting source and a first neutron detector adapted to be immersed in the aqueous slurry; the fast neutron emitting source and the first neutron detector being located at a predetermined fixed separation of from 1-8 cm. from one another;
- a second neutron detector, separated by a predetermined distance of from about 12 to about 20 cm. from the neutron source;
- means for relating the neutron counts determined by the first and second neutron detectors to the consistency of the slurry in which the neutron sources and the neutron detector are immersed, and to the density of the suspended material.

* * * * *